(12) United States Patent
Balakshin et al.

(10) Patent No.: US 9,150,729 B2
(45) Date of Patent: *Oct. 6, 2015

(54) DERIVATIVES OF NATIVE LIGNIN FROM SOFTWOOD FEEDSTOCKS

(71) Applicant: Lignol Innovations Ltd., Burnaby (CA)

(72) Inventors: Mikhail Yurevich Balakshin, North Vancouver (CA); Alex Berlin, Burnaby (CA); Humbert Thomas Dellicolli, Hanahan, SC (US); Chadrick Adam Nathaniel Jordan Grunert, Vancouver (CA); Vera Maximenko Gutman, Burnaby (CA); Darwin Ortiz, Delta (CA); Edward Kendall Pye, Media, PA (US)

(73) Assignee: FIBRIA INNOVATIONS INC., Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 14/188,495

(22) Filed: Feb. 24, 2014

(65) Prior Publication Data

US 2014/0206799 A1    Jul. 24, 2014

Related U.S. Application Data

(60) Continuation of application No. 13/829,608, filed on Mar. 14, 2013, now Pat. No. 8,696,865, which is a

(51) Int. Cl.
*C08H 7/00* (2011.01)
*C08L 23/02* (2006.01)
(Continued)

(52) U.S. Cl.
CPC ............... *C08L 97/005* (2013.01); *A23K 1/12* (2013.01); *A23L 1/3002* (2013.01); *A61K 36/15* (2013.01);
(Continued)

(58) Field of Classification Search
CPC ......... C08L 23/00; C08L 97/005; C08H 6/00; C07G 1/00
USPC ................................................ 162/14; 524/76
See application file for complete search history.

(56) References Cited

U.S. PATENT DOCUMENTS

| 4,764,596 A | 8/1988 | Lora et al. |
| 5,196,460 A | 3/1993 | Lora et al. |

(Continued)

FOREIGN PATENT DOCUMENTS

| CA | 2597135 A1 | 9/2008 |
| CN | 1189556 A | 8/1998 |

(Continued)

OTHER PUBLICATIONS

International Search Report for PCT/CA2008/001001, Filed on May 23, 2008, Applicant: Lignol Innovations Ltd. et al., Date of Mailing: Aug. 8, 2008, 4 pages.

(Continued)

*Primary Examiner* — John Uselding
(74) *Attorney, Agent, or Firm* — Perkins Coie LLP; Viola T. Kung

(57) ABSTRACT

The present invention relates to softwood lignin derivatives having an aliphatic hydroxyl content of from about 2.5 mmol/g to about 7 mmol/g lignin, and the preparation method thereof. The lignin derivatives have a desired antioxidant activity characterized by radical scavenging index (RSI). Another aspect of the invention relates to compositions comprising the softwood lignin derivative. Another aspect of the invention relates to a use of the softwood lignin derivatives comprising incorporating the softwood lignin derivatives into polymer compositions.

19 Claims, 2 Drawing Sheets

Related U.S. Application Data division of application No. 12/705,938, filed on Feb. 15, 2010, now Pat. No. 8,431,635.

(60) Provisional application No. 61/233,345, filed on Aug. 12, 2009, provisional application No. 61/182,044, filed on May 28, 2009.

(51) Int. Cl.

| | | |
|---|---|---|
| C08L 97/00 | (2006.01) | |
| A23K 1/12 | (2006.01) | |
| A23L 1/30 | (2006.01) | |
| A61K 36/15 | (2006.01) | |
| A61K 36/48 | (2006.01) | |
| A61K 36/54 | (2006.01) | |
| A61K 36/76 | (2006.01) | |
| C07G 1/00 | (2011.01) | |
| C08J 3/00 | (2006.01) | |
| C08K 5/13 | (2006.01) | |
| C09K 15/06 | (2006.01) | |

(52) U.S. Cl.
CPC .............. *A61K 36/48* (2013.01); *A61K 36/54* (2013.01); *A61K 36/76* (2013.01); *C07G 1/00* (2013.01); *C08H 6/00* (2013.01); *C08J 3/00* (2013.01); *C08K 5/13* (2013.01); *C08L 23/02* (2013.01); *C09K 15/06* (2013.01); *C08J 2397/00* (2013.01)

(56) References Cited

U.S. PATENT DOCUMENTS

| | | | |
|---|---|---|---|
| 5,681,427 A | 10/1997 | Lora et al. | |
| 6,555,350 B2 | 4/2003 | Ahring et al. | |
| 7,465,791 B1 | 12/2008 | Hallberg et al. | |
| 8,288,460 B2 | 10/2012 | Balakshin et al. | |
| 8,378,020 B1 | 2/2013 | Balakshin et al. | |
| 8,426,502 B2 | 4/2013 | Balakshin et al. | |
| 8,431,635 B2* | 4/2013 | Balakshin et al. | 524/76 |
| 8,445,562 B2 | 5/2013 | Balakshin et al. | |
| 8,696,865 B2* | 4/2014 | Balakshin et al. | 162/14 |
| 2001/0018956 A1 | 9/2001 | Stohrer et al. | |
| 2009/0117226 A1 | 5/2009 | Hallberg et al. | |
| 2010/0305241 A1 | 12/2010 | Balakshin et al. | |
| 2010/0305242 A1 | 12/2010 | Balakshin et al. | |
| 2010/0305244 A1 | 12/2010 | Balakshin et al. | |
| 2011/0236946 A1 | 9/2011 | Maclachlan et al. | |

FOREIGN PATENT DOCUMENTS

| | | |
|---|---|---|
| CN | 1275987 A | 12/2000 |
| CN | 101711229 A | 5/2010 |
| CN | 101711263 A | 5/2010 |
| EP | 0105937 A1 | 4/1984 |
| EP | 0737253 A1 | 10/1996 |
| EP | 2008661 A2 | 12/2008 |
| EP | 2150572 A1 | 2/2010 |
| EP | 2173889 A1 | 4/2010 |
| WO | 0075153 A2 | 12/2000 |
| WO | 2007129921 A1 | 11/2007 |
| WO | WO-2008144878 A1 | 12/2008 |
| WO | WO-2008144903 A1 | 12/2008 |
| WO | WO-2009003292 A1 | 1/2009 |
| WO | 2009028969 A1 | 3/2009 |
| WO | WO-2010060183 A1 | 6/2010 |
| WO | WO-2010081231 A1 | 7/2010 |

OTHER PUBLICATIONS

International Search Report for PCT/CA2010/000205, Filed on Feb. 15, 2010, Applicant: Lignol Innovations Ltd. et al., Date of Mailing: Jun. 1, 2010, 5 pages.
International Search Report for PCT/CA2010/000209, Filed on Feb. 15, 2010, Applicant: Lignol Innovations Ltd. et al., Date of Mailing: May 14, 2010, 4 pages.
International Search Report for PCT/CA2010/000210, Filed on Feb. 15, 2010, Applicant: Lignol Innovations Ltd. et al., Date of Mailing: May 31, 2010, 4 pages.
Argyropoulos, D.S. et al., "Isolation of Residual Kraft Lignin in High Yield and Purity," Journal of Pulp and Paper Science 2002, 28, 2, pp. 50-54.
Asgari, F. et al., "Fundamentals of oxygen delignification. Part II. Functional group formation/elimination in residual kraft lignin," Can. J. Chem. 1998, 76, pp. 1606-1615.
Cateto, C.A. et al., "Lignins as a Macromonomers for Polyurethane Synthesis: A Comparative Study on Hydroxyl Group Determination," Journal of Applied Polymer Science 2008, 109, pp. 3008-3017.
Catignani, G.L. et al., "Antioxidant Properties of Lignin," Journal of Food Science 1982, vol. 47, 2 pages.
Chakar, F.S. et al., "Biobleaching chemistry of laccase-mediator systems on high-lignin-content kraft pulps," Can. J. Chem. 2004, 82, pp. 344-352.
Chakar, F.S. et al., "Laccase-Lignin Reactions," IPST Technical Paper Series No. 876, Institute of Paper Science and Technology, Aug. 2000, 6 pages.
Colodette, J.L. et al., "Influence of pulping conditions on eucalyptus kraft pulp yield, quality, and bleachability," TAPPI Journal 2002, pp. 14-20.
Crestini, C. et al., "Structural Analysis of Wheat Straw Lignin by Quantitative 31P and 2D NMR Spectroscopy. The Occurrence of Ester Bonds and α-O-4 Substructures," J.Agric. Food Chem., 1997, 45, pp. 1212-1219.
Dizhbite, T. et al., "Characterization of the radical scavenging activity of lignins—natural antioxidants," Bioresource Technology 2004, 95, pp. 309-317.
Froass, P.M. et al., "Nuclear Magnetic Resonance Studies. 4. Analysis of Residual Lignin after Kraft Pulping," Ind. Eng. Chem. Res. 1998, 37, pp. 3388-3394.
Gellerstedt. G. et al., "Chemical Structures Present in Biofuel Obtained from Lignin," Energy & Fuels 2008, 22, pp. 4240-4244.
Gregorova, A. et al., "Stabilization effect of lignin in polypropylene and recycled polypropylene," Polymer Degradation and Stability 2005, 89, pp. 553-558.
Jaaskelainen, A.S. et al., "The effect of isolation method on the chemical structure of residual lignin," Wood Sci Technol 2003, 37, pp. 91-102.
Kasprzycka-Guttman, T., et al., "Antioxidant properties of lignin and its fractions," Thermochimica Acta 1994, 231, pp. 161-168.
Kosikova, B. et al., "Lignin-Stimulated Protection of Polypropylene Films and DNA in Cells of Mice against Oxidation Damage," BioResources May 2009, 4(2), pp. 805-815.
Kubo, S. et al., "Hydrogen Bonding in Lignin: A Fourier Transform Infrared Model Compound Study," Biomacromolecules 2005, 6, pp. 2815-2821.
Kubo, S. et al., "Kraft Lignin/Poly (ethylene oxide) Blends: Effect of Lignin Structure on Miscibility and Hydrogen Bonding," Journal of Applied Polymer Science 2005, 98, pp. 1437-1444.
Lucia, L.A. et al., "Comparative Evaluation of Oxygen Delignification Processes for Low- and High-Lignin-Content Softwood Kraft Pulps," Ind. Eng. Chem. Res. 2002, 41, pp. 5171-5180.
Megiatto, J.D. et al., "Sisal Fibers: Surface Chemical Modification Using Reagent Obtained from a Renewable Source; Characterization of Hemicellulose and Lignin as Model Study," J. Agric. Food Chem. 2007, 55, pp. 8576-8584.
Nieminen, M.O.J. et al., "Determination of Hydroxyl Groups in Kraft Pine Lignin by Silicon-29 NMR Spectroscopy," Holzforschung 1989, 43, pp. 303-307.
Pan et al., "Biorefining of Sotwoods Using Ethanol Organosolv Pulping"; Biotechnology and Bioengineering; vol. 90, No. 4 (May 20, 2005).
Pan et al., "Orgaosolv Ethanol Lignin from Hybrid Poplar as a Radical Scavenger: Relationship between Lignin Structure, Extraction Conditions, and Antioxidant Activity," J. Agric. Food Chem., 2006, 54, 5806-5813.

(56) References Cited

OTHER PUBLICATIONS

Pu, Y. et al., "Investigation of the photo-oxidative chemistry of acetylated softwood lignin," Journal of Photochemistry and Photobiology: A Chemistry 163, 2004, pp. 215-221.

Pu, Y. et al., "Structural analysis of acetylated hardwood lignins and their photoyellowing properties," Can. J. Chem. 2005, 83, pp. 2132-2139.

Sealey, J et al., "Residual Lignin Studies of Laccase Delignified Kraft Pulps," IPST Technical Paper Series, No. 621, Institute of Paper Science and Technology, Aug. 1996, 7 pages.

Tohmura, Shin-ichiro et al., "Determination of Arylglycerol-β-aryl Ethers and Other Linkages in Lignins Using DFRC/31P NMR," J. Agric. Food Chem. 2001, 49, pp. 536-542.

Vinardell, M.P. et al., "Potential applications of antioxidant lignins from different sources," Industrial Crops and Products 2008, pp. 220-223.

Wu, S. et al., "An Improved Method for Isolating Lignin in High Yield and Purity," Journal of Pulp and Paper Science, Jul. 2003, vol. 29, No. 7, pp. 235-240.

Yang, R. et al., "Oxygen Degradation and Spectroscopic Characterization of Hardwood Kraft Lignin," Ind. Eng. Chem. Res. 2002, 41, pp. 5941-5948.

Zawadzki, M. et al., "N-Hydroxy Compounds as New Internal Standards for the 31P-NMR Determination of Lignin Hydroxy Functional Groups," Holzforschung 2001, 55, 3, pp. 283-285.

Exhibit 1—document submitted by a 3rd party observation in corresponding European application No. 10779949.6, dated Feb. 15, 2010.
Exhibit 2—document submitted by a 3rd party observation in corresponding European application No. 10779949.6, dated Feb. 15, 2010.
Exhibit 3—document submitted by a 3rd party observation in corresponding European application No. 10779949.6, dated Feb. 15, 2010.
Exhibit 4—document submitted by a 3rd party observation in corresponding European application No. 10779949.6, dated Feb. 15, 2010.
Annex I, II and III—document submitted by a 3rd party observation in corresponding European application No. 10779949.6, dated Feb. 15, 2010.

Arlt, Herbert G. Jr., "Lignin Structure. VIII. Characterization of Ethanol Spruce Lignin Prepared by a New Method", Contribution from the State University of New York, College of Forestry, Chemistry Dept., 1956. pp. 1904-1906.

* cited by examiner

DERIVATIVES OF NATIVE LIGNIN FROM SOFTWOOD FEEDSTOCKS

This application is a continuation of U.S. application Ser. No. 13/829,608, filed Mar. 14, 2013; which is a divisional application of U.S. application Ser. No. 12/705,938, filed Feb. 15, 2010, now U.S. Pat. No. 8,431,635; which claims the benefit of U.S. Provisional Application Nos. 61/233,345, filed Aug. 12, 2009; and 61/182,044, filed May 28, 2009. The contents of the above-identified applications are incorporated herein by reference in their entireties.

FIELD

This invention relates to derivatives of native lignin recovered from softwood feedstocks, and industrial applications thereof. More particularly, this invention relates to derivatives of native lignin having certain chemical properties as well as uses, processes, methods, and compositions thereof.

BACKGROUND

Native lignin is a naturally occurring amorphous complex cross-linked organic macromolecule that comprises an integral component of all plant biomass. The chemical structure of lignin is irregular in the sense that different structural units (e.g., phenylpropane units) are not linked to each other in any systematic order. It is known that native lignin comprises pluralities of two monolignol monomers that are methoxylated to various degrees (trans-coniferyl alcohol and trans-sinapyl alcohol) and a third non-methoxylated monolignol (trans-p-coumaryl alcohol). Various combinations of these monolignols comprise three building blocks of phenylpropanoid structures i.e. guaiacyl monolignol, syringyl monolignol and p-hydroxyphenyl monolignol, respectively, that are polymerized via specific linkages to form the native lignin macromolecule.

Extracting native lignin from lignocellulosic biomass during pulping generally results in lignin fragmentation into numerous mixtures of irregular components. Furthermore, the lignin fragments may react with any chemicals employed in the pulping process. Consequently, the generated lignin fractions can be referred to as lignin derivatives and/or technical lignins. As it is difficult to elucidate and characterize such complex mixture of molecules, lignin derivatives are usually described in terms of the lignocellulosic plant material used, and the methods by which they are generated and recovered from lignocellulosic plant material, i.e. hardwood lignins, softwood lignins, and annual fibre lignins.

Native lignins are partially depolymerized during the pulping processes into lignin fragments which dissolve in the pulping liquors and subsequently separated from the cellulosic pulps. Post-pulping liquors containing lignin and polysaccharide fragments, and other extractives, are commonly referred to as "black liquors" or "spent liquors", depending on the pulping process. Such liquors are generally considered a by-product, and it is common practice to combust them to recover some energy value in addition to recovering the cooking chemicals. However, it is also possible to precipitate and/or recover lignin derivatives from these liquors. Each type of pulping process used to separate cellulosic pulps from other lignocellulosic components produces lignin derivatives that are very different in their physico-chemical, biochemical, and structural properties.

Given that lignin derivatives are available from renewable biomass sources there is an interest in using these derivatives in certain industrial applications. For example, lignin derivatives obtained via organosolv extraction, such as the Alcell® process (Alcell is a registered trademark of Lignol Innovations Ltd., Burnaby, BC, CA), have been used in rubber products, adhesives, resins, plastics, asphalt, cement, casting resins, agricultural products, oil-field products and as feedstocks for the production of fine chemicals.

However, large-scale commercial application of the extracted lignin derivatives, particularly those isolated in traditional pulping processes employed in the manufacture of pulp for paper production, has been limited due to, for example, the inconsistency of their chemical and functional properties. This inconsistency may, for example, be due to changes in feedstock supplies and the particular extraction/generation/recovery conditions. These issues are further complicated by the complexity of the molecular structures of lignin derivatives produced by the various extraction methods and the difficulty in performing reliable routine analyses of the structural conformity and integrity of recovered lignin derivatives. For instance, lignin derivatives are known to have antioxidant properties (e.g. Catignani G. L., Carter M. E., Antioxidant Properties of Lignin, Journal of Food Science, Volume 47, Issue 5, 1982, p. 1745; Pan X. et al. J. Agric. Food Chem., Vol. 54, No. 16, 2006, pp. 5806-5813) but, to date, these properties have been highly variable making the industrial application of lignin derivatives as an antioxidant problematic.

Thermoplastics and thermosets are used extensively for a wide variety of purposes. Examples of thermoplastics include classes of polyesters, polycarbonates, polylactates, polyvinyls, polystyrenes, polyamides, polyacetates, polyacrylates, polypropylene, and the like. Polyolefins such as polyethylene and polypropylene represent a large market, amounting to more than 100 million metric tons annually. During manufacturing, processing and use the physical and chemical properties of certain thermoplastics can be adversely affected by various factors such as exposure to heat, UV radiation, light, oxygen, mechanical stress or the presence of impurities. Clearly it is advantageous to mitigate or avoid these problems. In addition, the increase in recycling of material has led to an increased need to address these issues.

Degradation caused by free radicals, exposure to UV radiation, heat, light, and environmental pollutants are frequent causes of the adverse effects. A stabilizer such as an antioxidant, anti-ozonant, or UV block is often included in thermoplastic resins for the purpose of aiding in the production process and extending the useful life of the product. Common examples of stabilizers and antioxidants include amine types, phenolic types, phenol alkanes, phosphites, and the like. These additives often have undesirable or even unacceptable environmental, health and safety, economic, and/or disposal issues associated with their use. Furthermore, certain of these stabilizers/antioxidants can reduce the biodegradability of the product.

It has been suggested that lignin may provide a suitable polymeric natural antioxidant which has an acceptable toxicity, efficacy, and environmental profile. See, for example, A. Gregorova et al., Radical scavenging capacity of lignin and its effect on processing stabilization of virgin and recycled polypropylene, Journal of Applied Polymer Science 106-3 (2007) pp. 1626-1631; C. Pouteau et al. Antioxidant Properties of Lignin in Polypropylene, Polymer Degradation and Stability 81 (2003) 9-18. Despite the advantages of lignin, for a variety of reasons, it has not been adopted for widespread use as an antioxidant. For instance, it is often problematic to provide lignins that perform consistently in terms of antioxidant activity. Also, the processing of the lignin may introduce substances that are incompatible for use with chemicals such as polyolefins. Additionally, the cost of producing and/or purifying the lignin may make it uneconomic for certain uses.

SUMMARY

The present invention provides derivatives of native lignin from softwood sources having a certain aliphatic hydroxyl content. Surprisingly, it has been found that consistent and predictable antioxidant activity may be provided by selecting for derivatives of native lignin having certain aliphatic hydroxyl contents.

As used herein, the term "native lignin" refers to lignin in its natural state, in plant material.

As used herein, the terms "lignin derivatives" and "derivatives of native lignin" refer to lignin material extracted from lignocellulosic biomass. Usually, such material will be a mixture of chemical compounds that are generated during the extraction process.

DETAILED DESCRIPTION

Figure 1:
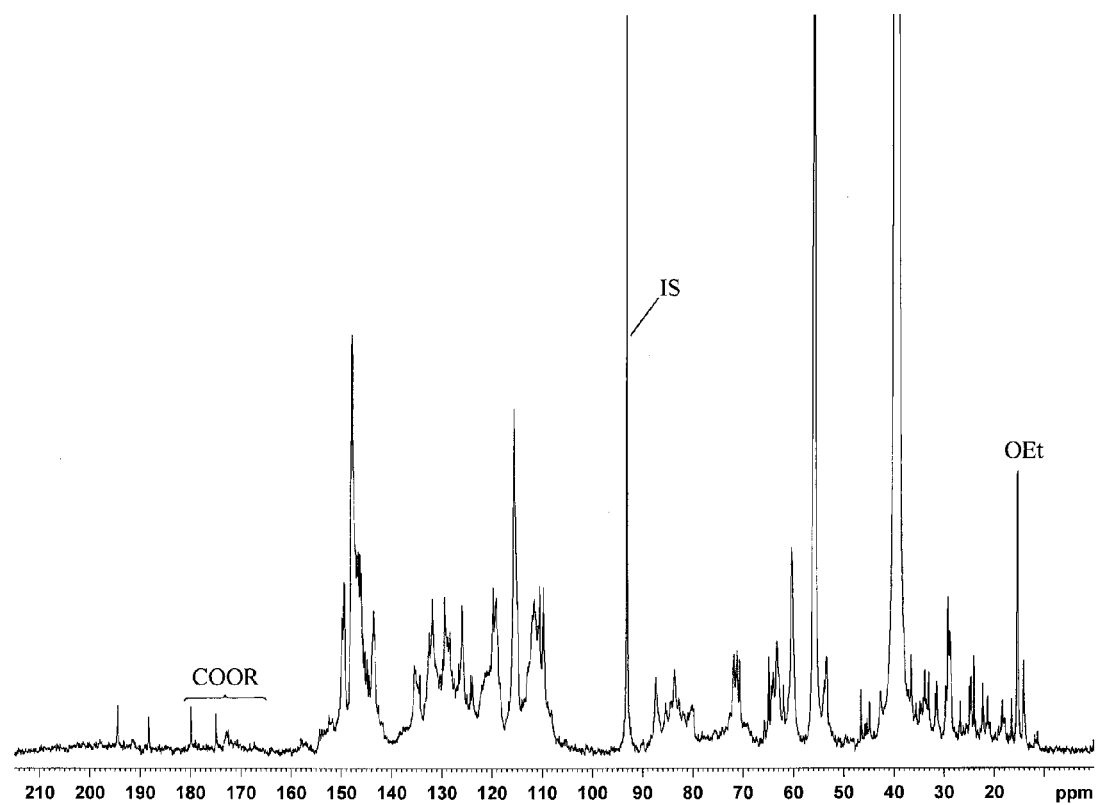
FIG. 1 shows the quantitative $^{13}$C NMR spectrum of non-acetylated softwood lignin derivatives.

The present invention provides derivatives of native lignin having certain aliphatic hydroxyl contents. It has been found that the aliphatic hydroxyl content of lignin derivatives can be correlated to the Radical Scavenging Index (RSI), a measure of antioxidant activity. Thus, selecting for derivatives of native lignin having a certain aliphatic hydroxyl content results in a product having a more consistent level of antioxidant activity. It has been found that derivatives of native lignin from softwood feedstocks having an aliphatic hydroxyl content of from about 2.5 mmol/g to about 7 mmol/g have a predictable level of antioxidant activity.

Radical Scavenging Index (RSI) is a measure of radical scavenging capacity. The assay uses 2,2-diphenyl-1-picryl-hydrazyl (DPPH), a stable free radical which absorbs light strongly at 515 nm, to measure a compound's radical scavenging index (RSI). In its radical form, DPPH• absorbs strongly at 515 nm and has a deep purple colour. As DPPH gives up its free electron to radical scavengers, it loses its purple colour and its absorbance shifts to 520 nm. The greater the drop in DPPH absorbance at 515 nm after a test compound has been added to the DPPH solution, the higher the compound's free RSI and also, its antioxidant activity. In the present invention, Vitamin E (Vit. E) and butylated hydroxytoluene (BHT) are used as positive controls. The lignin derivative samples (1.0-2.0 mg), Vit. E control samples (1.0-2.0 mg), and BHT control samples (6.0-8.0 mg) are prepared for testing by being placed into microcentrifuge tubes after which each was diluted with 1.0 mL of 90% (v/v) aqueous dioxan, vortexed, transferred to new microcentrifuge tubes and further diluted 50/50 with 90% aqueous dioxane to give stock concentrations of 0.5-1.0 mg/mL for samples and Vitamin E and 3.0-4.0 mg/mL for BHT. An indicating (purple) DPPH stable free radical solution is made by dissolving 3.78 mg DPPH in 100 mL 90% dioxane (95.9 µM). Samples and standards are serially diluted to fill columns of a quartz 96-well plate (8 dilutions). The assays are performed by placing aliquots of the sample stock solutions into two rows of wells in a 96-well plate. The first row served as the reference row while the second row received DPPH aliquots. 165 µL of 90% dioxane was added to each well and mixed. Aliquots of the mixed samples in each row are transferred to the adjacent row which is further diluted with 165 µL of 90% dioxane in each well. The mixing, transferring and dilution are repeated until the last row of wells is prepared. The same volume of aliquots is removed from the last row. The 96-well plate also contains a row of wells that received only the 90% dioxane. In the final step of the preparation procedure, 165 µL of the DPPH solution is added as quickly as possible to all the control and analytical columns by using an 8-channel autopipette and an Eppendorf® reagent reservoir. As soon as all reagents are added, the plate is placed into a plate-reading spectrophotometer (Spectra Max Plus, Molecular Devices, Sunnyvale, Calif., USA), and absorbance measurements are carried out. The program for the spectrophotometer (SOFTmax software) consists of a timing sequence of 16 min and a reading of the entire plate at 515 nm. RSI is defined as the inverse of the concentration which produces 50% inhibition in DPPH absorbance at 515 nm. The results are then 'normalized' by dividing the ample RSI by the RSI value for the BHT control. The normalized RSI is represented by this acronym "NRSI".

In the present invention, "aliphatic hydroxyl content" refers to the quantity of aliphatic hydroxyl groups in the lignin derivatives and is the arithmetic sum of the quantity of primary and secondary hydroxyl groups (OHal=OHpr+OHsec). The aliphatic hydroxyl content can be measured by quantitative $^{13}$C high resolution NMR spectroscopy of acetylated and non-acetylated lignin derivatives, using, for instance, 1,3,5-trioxane and tetramethyl silane (TMS) as internal reference. For the data analysis "BASEOPT" (DIGMOD set to baseopt) routine in the software package TopSpin 2.1.4 was used to predict the first FID data point back at the mid-point of $^{13}$C r.f. pulse in the digitally filtered data was used. For the NMR spectra recording a Bruker AVANCE II digital NMR spectrometer running TopSpin 2.1 was used. The spectrometer used a Bruker 54 mm bore Ultrashield magnet operating at 14.1 Tesla (600.13 MHz for $^1$H, 150.90 MHz for $^{13}$C). The spectrometer was coupled with a Bruker QNP cryoprobe (5 mm NMR samples, $^{13}$C direct observe on inner coil, $^1$H outer coil) that had both coils cooled by helium gas to 20K and all preamplifiers cooled to 77K for maximum sensitivity. Sample temperature was maintained at 300 K±0.1 K using a Bruker BVT 3000 temperature unit and a Bruker BCU05 cooler with ca. 95% nitrogen gas flowing over the sample tube at a rate of 800 L/h.

Quantification of ethoxyl groups was performed similarly to aliphatic hydroxyls quantification by high resolution $^{13}$C NMR spectroscopy. Identification of ethoxyl groups was confirmed by 2D NMR HSQC spectroscopy. 2D NMR spectra were recorded by a Bruker 700 MHz UltraShield Plus standard bore magnet spectrometer equipped with a sensitive cryogenically cooled 5 mm TCI gradient probe with inverse geometry. The acquisition parameters were as follow: standard Bruker pulse program hsqcetgp, temperature of 298 K, a 90° pulse, 1.1 sec pulse delay (d1), and acquisition time of 60 msec.

The present invention provides derivatives of native lignin recovered during or after pulping of lignocellulosic softwood feedstocks. The pulp may be from any suitable softwood feedstock.

Examples of softwood feedstocks include *Araucaria* (e.g. *A. cunninghamii, A. angustifolia, A. araucana*); softwood Cedar (e.g. *Juniperus virginiana, Thuja plicata, Thuja occidentalis, Chamaecyparis thyoides Callitropsis nootkatensis*); Cypress (e.g. *Chamaecyparis, Cupressus Taxodium, Cupressus arizonica, Taxodium distichum, Chamaecyparis obtusa,*

*Chamaecyparis lawsoniana, Cupressus semperviren*); Rocky Mountain Douglas fir; European Yew; Fir (e.g. *Abies balsamea, Abies alba, Abies procera, Abies amabilis*); Hemlock (e.g. *Tsuga canadensis, Tsuga mertensiana, Tsuga heterophylla*); Kauri; Kaya; Larch (e.g. *Larix decidua, Larix kaempferi, Larix laricina, Larix occidentalis*); Pine (e.g. *Pinus nigra, Pinus banksiana, Pinus contorta, Pinus radiata, Pinus ponderosa, Pinus resinosa, Pinus sylvestris, Pinus strobus, Pinus monticola, Pinus lambertiana, Pinus taeda, Pinus palustris, Pinus rigida, Pinus echinata*); Redwood; Rimu; Spruce (e.g. *Picea abies, Picea mariana, Picea rubens, Picea sitchensis, Picea glauca*); Sugi; and combinations/hybrids thereof.

For example, softwood feedstocks which may be used herein include cedar; fir; pine; spruce; and combinations thereof. The softwood feedstocks for the present invention may be selected from loblolly pine (*Pinus taeda*), radiata pine, jack pine, spruce (e.g., white, interior, black), Douglas fir, *Pinus silvestris, Picea abies*, and combinations/hybrids thereof. The softwood feedstocks for the present invention may be selected from pine (e.g. *Pinus radiata, Pinus taeda*); spruce; and combinations/hybrids thereof.

The present derivatives of native lignin from softwood feedstocks may have an aliphatic hydroxyl content of, for example, about 2.5 mmol/g or greater, about 2.6 mmol/g or greater, about 2.7 mmol/g or greater, about 2.8 mmol/g or greater, about 2.9 mmol/g or greater, about 3 mmol/g or greater.

The present derivatives of native lignin from softwood feedstocks may have an aliphatic hydroxyl content of, for example, about 7 mmol/g or less; about 6.5 mmol/g or less; about 6 mmol/g or less; about 5.8 mmol/g or less; about 5.6 mmol/g or less; about 5.5 mmol/g or less; about 5 mmol/g or less.

Derivatives of native lignin according to the present invention, coming from softwood feedstocks, may have a normalized RSI of, for example, from about 10 to about 40.

The derivatives of native lignin will vary with the type of process used to separate native lignins from cellulose and other biomass constituents. Preparations very similar to native lignin can be obtained by (1) solvent extraction of finely ground wood (milled-wood lignin, MWL) or by (2) acidic dioxane extraction (acidolysis) of wood. Derivatives of native lignin can be also isolated from biomass pre-treated using (3) steam explosion, (4) dilute acid hydrolysis, (5) ammonia fiber expansion, (6) autohydrolysis methods. Derivatives of native lignin can be recovered after pulping of lignocellulosics including industrially operated (3) kraft and (4) soda pulping (and their modifications) and (5) sulphite pulping. In addition, a number of various pulping methods have been developed but not industrially introduced. Among them four major "organosolv" pulping methods tend to produce highly-purified lignin mixtures. The first organosolv method uses ethanol/solvent pulping (aka the Alcell® process); the second organosolv method uses alkaline sulphite anthraquinone methanol pulping (aka the "ASAM" process); the third organosolv process uses methanol pulping followed by methanol, NaOH, and anthraquinone pulping (aka the "Organocell" process); the fourth organosolv process uses acetic acid/hydrochloric acid or formic acid pulping (aka the "Acetosolv" process).

It should be noted that kraft pulping, sulphite pulping, and ASAM organosolv pulping will generate derivatives of native lignin containing significant amounts of organically-bound sulphur which may make them unsuitable for certain uses. Acid hydrolysis, soda pulping, steam explosion, Alcell® pulping, Organocell pulping, and Acetosolv pulping will generate derivatives of native lignin that are sulphur-free or contain low amounts of inorganic sulphur.

Organosolv processes, particularly the Alcell® process, tend to be less aggressive and can be used to separate highly purified lignin derivatives and other useful materials from biomass without excessively altering or damaging the native lignin building blocks. Such processes can therefore be used to maximize the value from all the components making up the biomass. Organosolv extraction processes however typically involve extraction at higher temperatures and pressures with a flammable solvent compared to other industrial processes and thus are generally considered to be more complex and expensive.

A description of the Alcell® process can be found in U.S. Pat. No. 4,764,596 (herein incorporated by reference). The process generally comprises pulping or pre-treating a fibrous biomass feedstock with primarily an ethanol/water solvent solution under conditions that include: (a) 60% ethanol/40% water (w/w), (b) temperature of about 180° C. to about 210° C., (c) pressure of about 20 atm to about 35 atm, and (d) a processing time of 5 to 120 minutes. Native lignins are degraded during pulping and their derivatives are dissolved into the pulping liquor which also receives solubilised hemicelluloses, other saccharides, carbohydrate-degradation products such as furfural, 5-hydroxymethyl furfural, acetic, levulinic, formic, and other organic acids derived from carbohydrates and extractives such as lipophilic extractives, phenols, and tannins. Organosolv pulping liquors are often called "black liquors". The organic acids released by organosolv pulping significantly acidify the black liquors to pH levels of about 5 and lower. After separation from the cellulosic pulps produced during the pulping process, the derivatives of native lignin are recovered from the black liquors by depressurization followed by flashing with cold water which will cause the fractionated derivatives of native lignin to precipitate thereby enabling their recovery by standard solids/liquids separation processes. Various disclosures exemplified by U.S. Pat. No. 7,465,791 and PCT Patent Application Publication No. WO 2007/129921, describe modifications to the Alcell organosolv process for the purposes of increasing the yields of fractionated derivatives of native lignin recovered from fibrous biomass feedstocks during biorefining. Modifications to the Alcell organosolv process conditions included adjusting: (a) ethanol concentration in the pulping liquor to a value selected from a range of 35%-85% (w/w) ethanol, (b) temperature to a value selected from a range of 100° C. to 350° C., (c) pressure to a value selected from a range of 5 atm to 35 atm, and (d) processing time to a duration from a range of 20 minutes to about 2 hours or longer, (e) liquor-to-wood ratio of 3:1 to 15:1 or higher, (f) pH of the cooking liquor from a range of 1 to 6.5 or higher if a basic catalyst is used.

The present invention provides a process for producing derivatives of native lignin, said process comprising:

(a) pulping a fibrous biomass feedstock with an organic solvent/water solution, (b) separating the cellulosic pulps or pre-treated substrates from the pulping liquor or pre-treatment solution, (c) recovering derivatives of native lignin.

The organic solvent may be selected from short chain primary and secondary alcohols, such as methanol, ethanol, propanol, and combinations thereof. For example, the solvent may be ethanol. The liquor solution may comprise about 20%, by weight, or greater, about 30% or greater, about 50% or greater, about 60% or greater, about 70% or greater, of ethanol.

Step (a) of the process may be carried out at a temperature of from about 100° C. and greater, or about 120° C. and greater, or about 140° C. and greater, or about 160° C. and greater, or about 170° C. and greater, or about 180° C. and greater. The process may be carried out at a temperature of from about 300° C. and less, or about 280° C. and less, or about 260° C. and less, or about 240° C. and less, or about 220° C. and less, or about 210° C. and less, or about 205° C. and less, or about 200° C. and less.

Step (a) of the process may be carried out at a pressure of about 5 atm and greater, or about 10 atm and greater, or about 15 atm and greater, or about 20 atm and greater, or about 25 atm and greater, or about 30 atm and greater. The process may be carried out at a pressure of about 150 atm and less, or about 125 atm and less, or about 115 atm and less, or about 100 atm and less, or about 90 atm and less, or about 80 atm and less.

The fibrous biomass may be treated with the solvent solution of step (a) for about 1 minute or more, about 5 minutes or more, about 10 minutes or more, about 15 minutes or more, about 30 minutes or more. The fibrous biomass may be treated with the solvent solution of step (a) at its operating temperature for about 360 minutes or less, about 300 minutes or less, about 240 minutes or less, about 180 minutes or less, about 120 minutes or less.

The pH of the pulp liquor may, for example, be from about 1 to about 6, or from about 1.5 to about 5.5.

The weight ratio of liquor to biomass may be any suitable ratio. For example, from about 5:1 to about 15:1, from about 5.5:1 to about 10:1; from about 6:1 to about 8:1.

The present invention provides a process for producing a softwood lignin derivative having an aliphatic hydroxyl content of about 2.5 mmol/g to about 7 mmol/g. Said process comprises:
  a) pulping or pre-treating a fibrous biomass feedstock in a vessel with an organic solvent/water solvent solution to form a liquor, wherein:
    i. the solution comprises about 30% or greater, by weight, of organic solvent; and
    ii. the pH of the liquor is from about 1 to about 5.5;
  b) heating the liquor to about 100° C. or greater;
  c) raising the pressure in the vessel to about 5 atm or greater;
  d) maintaining the elevated temperature and pressure for 1 minute or longer;
  e) separating the cellulosic pulps from the pulp liquor
  f) recovering derivatives of native lignin.

The derivatives of native lignin herein may be incorporated into polymer compositions. The compositions herein may comprise a lignin derivative according to the present invention and a polymer-forming component. As used herein, the term 'polymer-forming component' means a component that is capable of being polymerized into a polymer as well as a polymer that has already been formed. For example, in certain embodiments the polymer-forming component may comprise monomer units which are capable of being polymerized. In certain embodiments the polymer component may comprise oligomer units that are capable of being polymerized. In certain embodiments the polymer component may comprise a polymer that is already substantially polymerized.

Polymers forming components for use herein may result in thermoplastic or thermoset polymers such as epoxy resins, urea-formaldehyde resins, phenol-formaldehyde resins, polyimides, and the like. For example, polyalkenes such as polyethylene or polypropylene.

Typically, the lignin derivative will comprise from about 0.1%, by weight, or greater, about 0.5% or greater, about 1% or greater, of the composition. Typically, the lignin derivative will comprise from about 80%, by weight, or less, about 60% or less, about 40% or less, about 20% or less, about 10% or less, of the composition.

The compositions comprise lignin derivative and polymer-forming component but may comprise a variety of other optional ingredients such as adhesion promoters; biocides (antibacterials, fungicides, and moldicides), anti-fogging agents; anti-static agents; bonding, blowing and foaming agents; dispersants; fillers and extenders; fire and flame retardants and smoke suppressants; impact modifiers; initiators; lubricants; micas; pigments, colorants and dyes; plasticizers; processing aids; release agents; silanes, titanates and zirconates; slip and anti-blocking agents; stabilizers; stearates; ultraviolet light absorbers; foaming agents; defoamers; hardeners; odorants; deodorants; antifouling agents; viscosity regulators; waxes; and combinations thereof.

The present invention provides the use of the present derivatives of native lignin as an antioxidant. For example, the present use may be as an antioxidant additive for use with thermoplastic polymers such as polyethylene, polypropylene, polyamides, styrene-butadiene, natural rubber, and combinations thereof.

The present invention provides methods of producing softwood derivatives of native lignin having an aliphatic hydroxyl content of about 2.5 mmol/g to about 7 mmol/g.

The present invention provides methods of producing softwood derivatives of native lignin having a normalized RSI of 5 or greater, 10 or greater, 12 or greater, 15 or greater.

The present invention provides methods of producing softwood derivatives of native lignin having a normalized RSI of 40 or less, 38 or less, 35 or less.

The present invention provides lignin derivatives comprising alkoxy groups. For example, the present lignin derivatives may have an alkoxy content of 2 mmol/g or less; about 1.4 mmol/g or less; about 1.2 mmol/g or less; about 1 mmol/g or less; about 0.8 mmol/g or less; about 0.7 mmol/g or less; about 0.6 mmol/g or less; about 0.5 mmol/g or less; about 0.4 mmol/g or less; about 0.3 mmol/g or less. The present lignin derivatives may have an alkoxy content of 0.001 mmol/g or greater, about 0.01 mmol/g of greater, about 0.05 mmol/g or greater, about 0.1 mmol/g or greater.

The present invention provides lignin derivatives comprising ethoxyl groups. For example, the present lignin derivatives may have an ethoxyl content of 2 mmol/g or less; about 1.4 mmol/g or less; about 1.2 mmol/g or less; about 1 mmol/g or less; about 0.8 mmol/g or less; about 0.7 mmol/g or less; about 0.6 mmol/g or less; about 0.5 mmol/g or less; about 0.4 mmol/g or less; about 0.3 mmol/g or less. The present lignin derivatives may have an ethoxyl content of 0.001 mmol/g or greater, about 0.01 mmol/g of greater, about 0.05 mmol/g or greater, about 0.1 mmol/g or greater.

The present lignin derivatives may have any suitable phenolic hydroxyl content such as from about 2 mmol/g to about 8 mmol/g. For example, the phenolic hydroxyl content may be from about 2.5 mmol/g to about 7 mmol/g; about 3 mmol/g to about 6 mmol/g.

The present lignin derivatives may have any suitable number average molecular weight (Mn). For example, the Mn may be from about 200 g/mol to about 3000 g/mol; about 350 g/mol to about 2000 g/mol; about 500 g/mol to about 1500 g/mol.

The present lignin derivatives may have any suitable weight average molecular weight (Mw). For example, the Mw may be from about 500 g/mol to about 5000 g/mol; about 750 g/mol to about 4000 g/mol; about 900 g/mol to about 3500 g/mol.

The present lignin derivatives may have any suitable polydispersity (D). For example, the D may be from about 1 to about 5; from about 1.2 to about 4; from about 1.3 to about 3.5; from about 1.4 to about 3.

The present lignin derivatives are preferably hydrophobic. Hydrophobicity may be assessed using contact angle measurements.

It has been suggested that lignins or lignin derivatives may be used in nutritional supplements (e.g. Baurhoo et. al., Purified Lignin: Nutritional and Health Impacts on Farm Animals—A Review, Animal Feed Science and Technology 144 (2008) 175-184). The present derivatives of native lignin may be used in nutritional supplements, nutraceuticals, functional foods, and the like. The stable and consistent antioxidant activity may be advantageous when formulating such compositions.

The present derivatives of native lignin may be used for other purposes such as, for example, laminates, stains, pigments, inks, adhesives, coatings, rubbers, elastomers, plastics, films, paints, carbon fibre composites, panel boards, print-circuit boards, lubricants, surfactants, oils, animal feed, food and beverages, and the like.

EXAMPLES

Example 1

Recovery of Lignin Derivatives from Hardwood Feedstocks

Softwood feedstock chips were prepared from: (1) hybrid spruce trees grown in British Columbia, (2) radiata pine grown in Chile, and (3) loblolly pine grown in Southeastern USA. Four samples of the hybrid spruce woodchips were individually pulped using an acid-catalysed ethanol organosolv pulping process wherein a different set of pulping conditions was used for each sample (Table 1). Process conditions for pulping four samples of the radiata pine chips are shown in Table 2. Process conditions for pulping four samples of the loblolly pine chips are shown in Table 3.

TABLE 1

Pulping conditions for hybrid spruce wood chip samples at 6:1 liquor-to-wood ratio.

| Run # | pH | Acid % | Time min | Temperature ° C. | Ethanol % | PL % |
|---|---|---|---|---|---|---|
| 1 | 1.95 | 1.90 | 33 | 179 | 57 | 63.89 |
| 2 | 2.18 | 0.90 | 55 | 184 | 47 | 40.42 |
| 3 | 1.81 | 2.50 | 36 | 175 | 78 | 71.84 |
| 4 | 2.12 | 1.20 | 41 | 181 | 68 | 70.59 |

TABLE 2

Pulping conditions for radiata pine wood chip samples at 6:1 liquor-to-wood ratio.

| Run # | pH | Acid % | Time min | Temperature ° C. | Ethanol % | PL % |
|---|---|---|---|---|---|---|
| 1 | 1.92 | 1.90 | 33 | 179 | 57 | 48.76 |
| 2 | 2.23 | 0.90 | 55 | 184 | 47 | 38.00 |
| 3 | 2.50 | 0.47 | 57 | 194 | 61 | 48.55 |
| 4 | 2.63 | 0.23 | 110 | 191 | 44 | 27.01 |

TABLE 3

Pulping conditions for loblolly pine wood chip samples at 6:1 liquor-to-wood ratio.

| Run # | pH | Acid % | Time min | Temperature ° C. | Ethanol % | PL % |
|---|---|---|---|---|---|---|
| 1 | 1.83 | 2.10 | 39 | 170 | 46 | 29.8 |
| 2 | 2.52 | 0.35 | 79 | 198 | 42 | 16.4 |
| 3 | 2.50 | 0.38 | 73 | 189 | 54 | 39.3 |
| 4 | 3.20 | 0.13 | 53 | 199 | 73 | 23.3 |

For each wood chips sample, the ethanol pulping solvent was prepared to the specified concentration by first, partially diluting the ethanol with water after which, a suitable amount of sulphuric acid was added to achieve the target final acidity. Finally, the ethanol solution was further diluted with water to achieve the target ethanol concentration.

The original lignin content of each fibrous biomass sub-sample was determined using the methods described in National Renewable Energy Laboratory (NREL) Technical Report entitled "Determination of Structural Carbohydrates and Lignin in Biomass"—Laboratory Analytical Procedure (TP-510-42618 (25 Apr. 2008)). Then, after adding the fibrous biomass sample to a pressure vessel (2 L or 7 L Parr reactor (Parr Instrument Company, Moline, Ill., USA)) (100-700 g odw chips), the pH-adjusted ethanol-based pulping solvent was added to the vessel at a 6:1 liquor:wood ratio & the pH recorded. The vessel was then pressurized and brought up to the target temperature listed in Tables 1-3 (spruce, radiata pine, loblolly pine, respectively). The biomass sample was then "cooked" for the specified period of time, after which, the pulping process was stopped. After pulping, the contents of pressure vessel were transferred to a hydraulic 20 ton manual shop press (Airco, China). The liquor was separated from the solids by first squeezing the pulped materials in the press to express the liquor. The expressed liquor was then filtered through a coarse silk screen to separate expressed chip residues from liquor stream. Next, fine particles were separated out from the liquor stream by filtration through fine filter paper (Whatman No 1). The recovered fine particles represent lignin derivatives that were extracted and self-precipitated out from the liquor during cooling of the pulped biomass. The particulate lignin is herein referred to as self-precipitated lignin derivatives (i.e., "SPL"). The solubilized lignin derivatives still remaining in the filtered liquor were precipitated from by dilution with cold water. The lignin derivatives precipitated by dilution with cold water are referred to as precipitated lignin or "PL". After determination of the dry weights of SPL and PL lignin derivatives, the relative yield of each lignin derivative was determined in reference to total lignin (sum of the Klason lignin (acid-insoluble lignin) and acid-soluble lignin) value determined for the original biomass sample before pulping. The yield of PL lignin derivatives for each sample is shown in Tables 1-3 on a weight % basis relative to their original lignin (Klason plus acid-soluble lignin values).

Example 2

Characterization of the Aliphatic Hydroxyl Content of Lignin Derivatives Recovered from Three Softwood Species Functionalized lignin derivatives recovered from hardwood biomass samples as described above, were analyzed to determine the content of primary hydroxyl groups mmol/g sample (OH-pr mmol/g) and content of secondary hydroxyl groups mmol/g sample (OH-sec mmol/g). These values were then used to calculate mmol aliphatic hydroxyl groups/g sample (OH-al mmol/g).

The hydroxyl contents were determined by quantitative $^{13}$C NMR spectroscopy on a Bruker 600 MHz spectrometer equipped with Cryoprobe at 300 K using ca 30% solutions of sample in DMSO-$d_6$. Chemical shifts were referenced to TMS (0.0 ppm). To ensure more accurate baseline, especially in the carbonyl region (215-185 ppm), the spectra were recorded in the interval 240-(−40) ppm. The following conditions were provided for the quantitative $^{13}$C-NMR:
1. Inverse gate detection;
2. a 90° pulse;
3. Complete relaxation of all nuclei was achieved by addition of chromium (III) acetylacetonate (0.01 M) and using a 1.2 s acquisition time and 1.7 s relaxation delay acquisition parameters.

The NMR spectra were Fourier-transformed, phased, calibrated using TMS signals as a reference (0 ppm), and the baseline was corrected by using a polynomial function. The correction of baseline was done using the following interval references to be adjusted to zero: (220-215 ppm)-(185-182 ppm)-(97-92 ppm)-(5-(−20)ppm). No other regions were forced to 0. The signals in the quantitative $^{13}$C NMR spectra were assigned on the basis of 2D HSQC spectra and a known database. The spectra were integrated then using the area of the internal standard (IS), trioxane, as the reference. Each spectrum was processed (as described) at least twice to ensure good reproducibility of the quantification. Some carboxyl and ester groups resonate in the resonance area of hydroxyl groups (171.5-166.5 ppm) in the spectra of acetylated lignins. The amounts of carboxyl and ester groups resonated in the interval of 171.5-166.5 ppm were determined from the spectra of non-acetylated lignins. The corrected content of hydroxyl groups was obtained then by deduction of the amounts of the carboxyl and ester groups from the corresponding resonances of hydroxyl groups (Table 4). The calculation of the quantity of the specific moieties was done as follows:

For non-acetylated lignins: $X(\text{mmol/g lignin}) = I_X \ast m_{IS} / (30 m_{Lig} \ast I_{IS}) \ast 1000$ For acetylated lignins: $X(\text{mmol/g lignin}) = I_X \ast m_{IS} / (30 m_{Lig} \ast I_{IS} - 42 \ast I_{OHtotal} \ast m_{IS}) \ast 1000$ Where X was the amount of the specific moiety; $I_X$, $I_{IS}$ and $I_{OHtotal}$ were the resonance values of the specific moiety (Table 4), the internal standard and total OH groups, correspondingly; $m_{Lig}$ and $m_{IS}$ are the masses of the lignin and internal standard.

Figure 2:
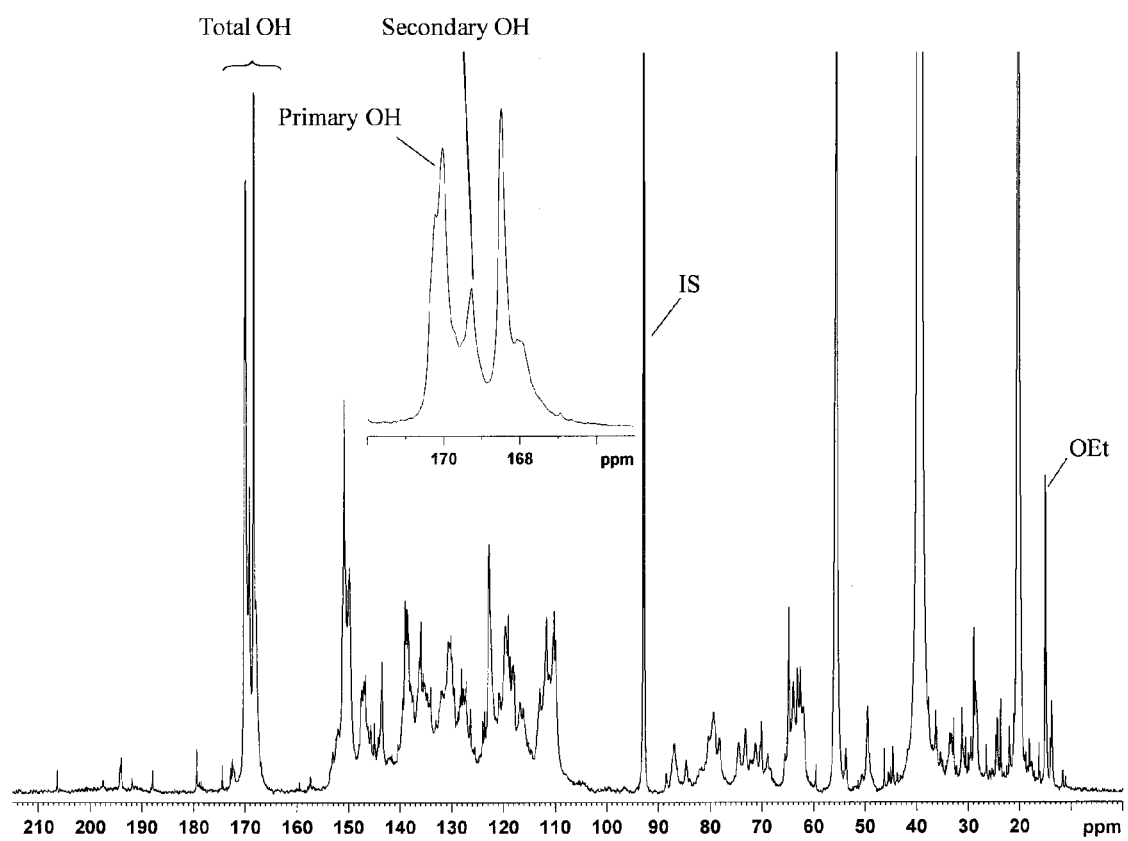
FIG. 2 shows the quantitative $^{13}$C NMR spectrum of acetylated softwood lignin derivatives.

The recorded NMR spectroscopic data are processed and graphically illustrated as shown in FIGS. 1 and 2. FIG. 1 shows the Quantitative $^{13}$C NMR Spectrum of non-acetylated softwood lignin derivatives. FIG. 2 shows the Quantitative $^{13}$C NMR Spectrum of acetylated softwood lignin derivatives.

TABLE 4

| Symbol | $I_X$ in Calculation Equation | Analytical Method |
|---|---|---|
| OH-pr mmol/g | Resonance at 171.5-169.7 ppm in the quantitative $^{13}$C NMR spectra of acetylated lignins minus resonance at 171.5-169.7 ppm in the quantitative $^{13}$C NMR spectra of non-acetylated lignins | Quantitative $^{13}$C High Resolution NMR of lignin using 1,3,5-trioxane as internal reference |
| OH-sec mmol/g | Resonance at 169.7-169.2 ppm in the quantitative $^{13}$C NMR spectra of acetylated lignins minus resonance at 169.7-169.2 ppm in the quantitative $^{13}$C NMR spectra of non-acetylated lignins | Quantitative $^{13}$C High Resolution NMR of lignin using 1,3,5-trioxane as internal reference |
| OH-total mmol/g | Resonance at 171.5-165.0 ppm in the quantitative $^{13}$C NMR spectra of acetylated lignins minus resonance at 171.5-166.5 ppm in the quantitative $^{13}$C NMR spectra of non-acetylated lignins | Quantitative $^{13}$C High Resolution NMR of lignin using 1,3,5-trioxane as internal reference |
| OH-al mmol/g | OH-al = OH-pr + OH-sec | |
| OEt mmol/g | Resonance at 16.0-14.5 ppm in the quantitative $^{13}$C NMR spectra (both in acetylated and non-acetylated lignins, calculated as average) | Quantitative $^{13}$C High Resolution NMR of lignin using 1,3,5-trioxane as internal reference combined with 2D HSQC |

The aliphatic hydroxyl contents of the PL lignin derivatives from each of the five samples of spruce woodchips are shown in Table 5. The contents ranged from 2.60 mmol/g in sample 1 to 3.04 mmol/g in sample 5.

TABLE 5

Aliphatic hydroxyl content and normalized radical scavenging index of PL lignins recovered from hybrid spruce woodchips.

| Run # | OH-pr mmol/g | OH-sec mmol/g | OH-al mmol/g | NRSI |
|---|---|---|---|---|
| 1 | 2.05 | 0.55 | 2.60 | 27.43 |
| 2 | 2.19 | 0.48 | 2.66 | 28.15 |
| 3 | 2.18 | 0.56 | 2.75 | 26.23 |
| 4 | 2.35 | 0.69 | 3.04 | 30.64 |

The aliphatic hydroxyl contents of the PL lignin derivatives from each of the four samples of radiata pine woodchips are shown in Table 6. The contents ranged from 0.76 mmol/g in sample 1 to 2.31 mmol/g in sample 4.

TABLE 6

Aliphatic hydroxyl content and normalized radical scavenging index of
PL lignins recovered from radiata pine woodchips.

| Run # | OH-pr mmol/g | OH-sec mmol/g | OH-al mmol/g | NRSI |
|---|---|---|---|---|
| 1 | 2.31 | 0.49 | 2.80 | 36.97 |
| 2 | 2.62 | 0.69 | 3.31 | 28.28 |
| 3 | 2.94 | 0.72 | 3.66 | 27.19 |
| 4 | 2.72 | 1.06 | 3.78 | 29.76 |

The aliphatic hydroxyl contents of the PL lignin derivatives from each of the four samples of loblolly pine chips are shown in Table 7. The contents ranged from 2.65 mmol/g in sample 1 to 3.81 mmol/g in sample 4.

TABLE 7

Aliphatic OH content and NRSI of PL lignins recovered
from loblolly pine woodchips.

| Run # | OH-pr mmol/g | OH-sec mmol/g | OH-al mmol/g | NRSI |
|---|---|---|---|---|
| 1 | 2.19 | 0.45 | 2.65 | 27.78 |
| 2 | 2.19 | 0.71 | 2.90 | 27.95 |
| 3 | 2.58 | 0.84 | 3.42 | 27.78 |
| 4 | 2.65 | 1.16 | 3.81 | 24.56 |

Example 3

Characterization of the NRSI of Lignin Derivatives Recovered from Three Softwood Species The lignin derivatives samples produced above were assessed for their radical scavenging index (RSI). The potential antioxidant activity of each PL lignin derivative was determined by measuring its radical savaging capacity. The assay used 2,2-diphenyl-1-picrylhydrazyl (DPPH), a stabile free radical which absorbs light strongly at 515 nm to measure a compound's radical scavenging index (RSI). In its radical form, DPPH• absorbs strongly at 515 nm and has a deep purple colour. As DPPH gives up its free electron to radical scavengers, it loses its purple colour and its absorbance shifts to 520 nm. The greater the drop in DPPH absorbance at 515 nm after a test compound has been added to the DPPH solution, the higher the compound's free RSI and also, its antioxidant activity. In the present study, Vit. E and BHT were used as positive controls. HPLY lignin derivative subsamples (1.0-2.0 mg), Vit. E control samples (1.0-2.0 mg), and BHT control samples (6.0-8.0 mg) were prepared for testing by being placed into epitubes after which, each was diluted with 1.0 mL of 90% (v/v) aqueous dioxan, vortexed, transferred to new epitubes and then further diluted 50/50 with 90% aqueous dioxane to give stock concentrations of 0.5-1.0 mg/mL for samples and Vitamin E and 3.0-4.0 mg/mL for BHT. An indicating (purple) DPPH stable free radical solution is made by dissolving 3.78 mg DPPH in 100 mL 90% dioxane (95.9 µM). Samples and standards are serial diluted to fill columns of a quartz 96-well plate (8 dilutions). The assays were performed by placing aliquots of the sample stock solutions into two rows of wells in a 96-well plate. The first row served as the reference row while the second row received DPPH aliquots. 165 µL of 90% dioxane was added to each well and mixed. Aliquots of the mixed samples in each row were transferred to the adjacent row and further diluted with 165 µL of 90% dioxane in each well. The mixing, transferring and dilution were repeated until the last row of wells is prepared. The same volume of aliquots was removed from the last row. The 96-well plate also contained a row of wells that received only the 90% dioxane. In the final step of the preparation procedure, 165 µL of the DPPH solution was added to all the control and analytical columns by using an 8-channel autopipette and an Eppendorf® reagent reservoir as quickly as possible. As soon as all reagents are added, the plate is placed into a plate-reading spectrophotometer (Molecular Devices, Sunnyvale, Calif., USA, Spectra Max Plus), and absorbance measurements are commenced. The program for the spectrophotometer (SOFTmax software) consisted of a timing sequence of 16 min and a reading of the entire plate at 515 nm. RSI (radical scavenging index) is defined as the inverse of the concentration which that produced 50% inhibition in DPPH absorbance at 515 nm. The results were then 'normalized' (NRSI) by dividing the sample RSI by the RSI value for the BHT control.

The NRSI values for lignin derivatives recovered from hybrid spruce woodchips are shown in Table 5. The NRSI values for lignin derivatives recovered from radiata pine woodchips are shown in Table 6. The NRSI values for lignin derivatives recovered from loblolly pine woodchips are shown in Table 7.

The invention claimed is:

1. A softwood lignin derivative recovered from a pulping process of a lignocellulosic biomass, said softwood lignin derivative having an aliphatic hydroxyl content of from about 2.5 mmol/g to about 7 mmol/g, a weight average molecular weight of from about 500 g/mol to about 5000 g/mol, a phenolic hydroxyl content of from about 2 mmol/g to about 8 mmol/g, and a normalized RSI of 10 or greater.

2. The lignin derivative according to claim 1, wherein the pulping process is selected from the group consisting of: steam explosion, dilute acid hydrolysis, ammonia fiber expansion, autohydrolysis, kraft and modifications thereof, soda pulping and modifications thereof, sulphite pulping, and organosolv processes.

3. The lignin derivative according to claim 1, wherein the pulping process is a sulphite process, a kraft process or modifications thereof.

4. The lignin derivative according to claim 1, wherein the wherein the lignin derivative has a polydispersity of from about 1 to about 5.

5. The lignin derivative according to claim 1, wherein the derivative has an aliphatic hydroxyl content of from about 2.75 mmol/g to about 5 mmol/g.

6. The lignin derivative according to claim 1, wherein the lignin is derived from biomass comprising pine, spruce, or combinations/hybrids thereof.

7. The lignin derivative according to claim 1, wherein the lignin is derived from biomass comprising *Pinus radiata*, *Pinus taeda*, spruce, or combinations/hybrids thereof.

8. The lignin derivative according to claim 1, having a normalized RSI of about 15 or greater.

9. A composition comprising the lignin derivative of claim 1 and a polymer-forming component.

10. A thermoplastic composition comprising the lignin derivative according to claim 1.

11. A polyolefin composition comprising the lignin derivative according to claim 1.

12. A method of producing a softwood lignin derivative, said method comprising:
 pulping a fibrous biomass;
 heating the biomass;
 maintaining the elevated temperature for 1 minute or longer;

separating the cellulosic pulp to form a lignin rich material; and recovering derivatives of native lignin wherein the derivatives have an aliphatic hydroxyl content of from 2.5 mmol/g to about 7 mmol/g, phenolic hydroxyl content of from about 2 mmol/g to about 8 mmol/g, and a normalized RSI of 10 or greater;

wherein the pulping is a sulphite process.

13. The method according to claim 12, wherein the derivative has an aliphatic hydroxyl content of from about 2.75 mmol/g to about 5 mmol/g.

14. The method according to claim 12, wherein the fibrous biomass comprises pine, spruce, or combinations/hybrids thereof.

15. The method according to claim 12, wherein the fibrous biomass comprises *Pinus radiata, Pinus taeda*, spruce, or combinations/hybrids thereof.

16. The method according to claim 12, wherein the lignin derivative has a polydispersity of from about 1 to about 5.

17. The method according to claim 12, wherein the derivative has an alkoxy content of 0.1 mmol/g or greater.

18. The method according to claim 1, wherein the derivative has a normalized RSI of 15 or greater.

19. The method according to claim 1, wherein the derivative has a normalized RSI of 40 or less.

* * * * *